US005366475A

United States Patent [19]

Voss et al.

[11] Patent Number: 5,366,475

[45] Date of Patent: Nov. 22, 1994

[54] TRAGUS ACUPRESSURE CLIP

[75] Inventors: Theodore N. Voss; Barbara Curran; Karl D. Kirk, III; Ellen R. Cohen, all of New York, N.Y.

[73] Assignee: Shatzu Health Products, Inc., New York, N.Y.

[21] Appl. No.: 994,195

[22] Filed: Dec. 21, 1992

[51] Int. Cl.[5] .......... A61B 17/00

[52] U.S. Cl. .......... 606/204

[58] Field of Search .......... 606/204, 201, 151, 157; 24/489, 487, 499, 511; 128/907

[56] References Cited

U.S. PATENT DOCUMENTS 3,456,262 7/1969 Coon .......... 24/511
4,319,574 3/1982 Sun et al. .......... 606/204

OTHER PUBLICATIONS

Brochure entitled, "Ancient Chinese Secret for Losing Weight Finally Revealed", Health Care Research Co., Patternson, N.J..

Brochure entitled, "The Nulife Ear Clip", Nulife Corp. 1990.

1992 Advertisement in "A Mail Order Fun Catalogue, and Manual for Chinese Weight Loss Earring", Johnson Smith Co. of Bradenton, Fla.

*Primary Examiner*—Tamara L. Graysay
*Attorney, Agent, or Firm*—Meltzer, Lippe, Goldstein, Wolfe, Schlissel & Sazer

[57] ABSTRACT

A clip is disclosed which is attached to the tragus lobe of the ear. The clip has a concave spring with two opposing jaws separated by a slot delineated by an inner surface of the concave spring. The clip also has two opposing pressure pads, each positioned on the end of a different jaw, on the inner surface of the spring, so that they are separated by an opening of the slot. The ear clip additionally has two finger tabs, each having one end attached to an end of a different jaw, on an outer surface of the spring and a second end extending away from the end of the jaw, along the outer surface of the spring.

25 Claims, 2 Drawing Sheets

TRAGUS ACUPRESSURE CLIP

FIELD OF THE INVENTION

The present invention relates to acupressure devices. More particularly, the present invention relates to an ear clip which is placed on the tragus lobe of the ear in order to stimulate nerve endings.

BACKGROUND OF THE INVENTION

Acupressure, i.e., the application of pressure to specific topical locations of the body, has been used to control weight loss and to reduce the urge to smoke. It has been proposed that the application of light pressure to the tragus lobe (small cartilage lobe which partially eclipses the opening to the ear canal) slows peristalsis (the wave-like contractions of the intestine). The brain, in turn, may interpret this effect as being caused by a half full stomach. Thus, appetite is reduced. The control of the desire to smoke is less well understood.

The prior art has proposed acupressure ear clips. One ear clip is disclosed in a brochure distributed by Health Care Research, a company located in Patterson, N.J. This ear clip is designed to be secured to the auricle (the external cartilage portion of the ear which projects from the head). A second ear clip is disclosed in a 1990 brochure distributed by Nulife Corp. The Nulife clip is designed for attachment to the tragus and has a single padded arm which is positioned in the ear canal. A third "Chinese Weight Loss Earring" is disclosed in a 1992 "Mail Order Fun" catalogue distributed by the Johnson Smith Company located in Bradenton, Fla. The weight loss earring is an approximately circular shaped plastic device which fits loosely around the auricle and which may be manually squeezed periodically (using the fingers) to pinch the auricle, It is an object of the present invention to provide a tragus clip which is comfortable to wear. It is another object of the present invention to provide an ear clip which is easy to attach to the tragus. It is also an object of the present invention to provide a tragus clip which supplies sufficient pressure to remain attached to the tragus yet is comfortable for use by a large segment of the population. It is further object of the present invention to provide a tragus clip which is easy to manufacture.

SUMMARY OF THE INVENTION

These and other objects are achieved by the present invention which provides a tragus clip having a concave shaped spring. The spring has two opposing jaws separated by a slot which is delineated by an inner surface of the spring. Two opposing pressure pads are also provided, each positioned at the end of a different jaw on the inner surface of the spring. In addition, two finger tabs are provided, each of which has one end attached to a different jaw on an outer surface of the spring. Each finger tab has a second end which extends away from the respective jaw to which the finger tab is attached along the outer surface of the spring. Thus, if the second ends of the finger tabs are urged towards one another, the jaws separate and the slot separating the pressure pads widens.

A tragus clip according to the present invention is simple yet can be easily made to precise tolerances. Furthermore, the finger tabs provide for good manual control for holding the clip in an opened position while it is positioned on the tragus yet have a small profile so that they can fit in the ear canal without touching it. Alternatively, the finger tabs may be omitted in an illustrative embodiment.

DETAILED DESCRIPTION OF THE INVENTION

Figure 1A:
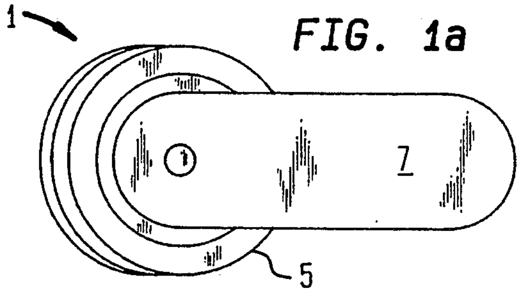
FIGS. 1*a*, 1*b* and 1*c* show a side, top and rear view, respectively, of an embodiment of a tragus clip according to the present invention.
Figure 1B:
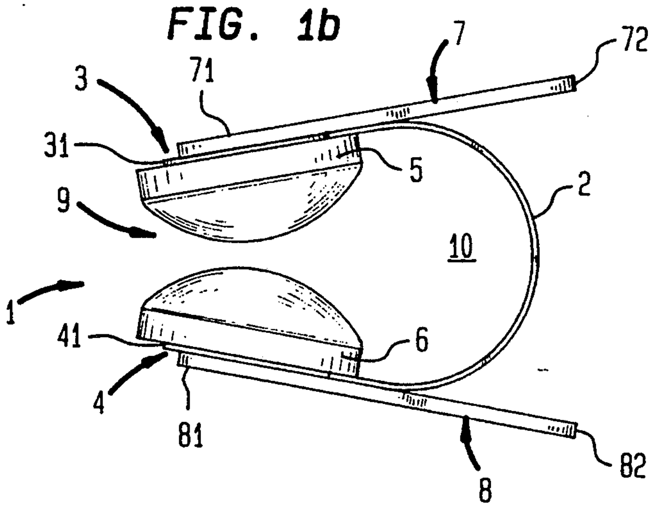
Figure 1C:
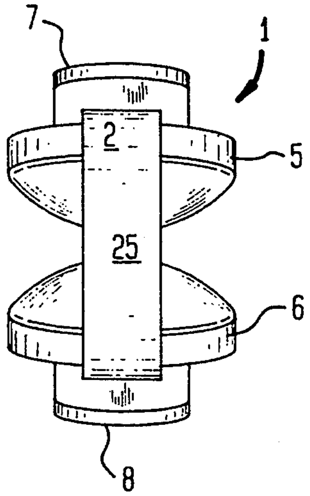

Referring now to FIGS. 1*a*, 1*b* and 1*c*, a tragus clip 1 according to the present invention is depicted. The tragus clip 1 includes a concave spring 2 having jaws 3 and 4. The spring 2 has an outer concave surface portion 25 on which graphic or textual information, such as a company logo, may be printed. Two pressure pads 5 and 6 are positioned on an inner, concave surface of the spring 2 at the end 31 or 41 of each jaw 3 or 4, respectively. The tragus clip 1 also has finger tabs 7 and 8 connected on one end 71 or 81 to the end 31 or 41 of the jaws 3 or 4, respectively, on an outer, convex surface of the spring 2. In an illustrative embodiment, however, the finger tabs may be omitted. The finger tabs 7 and 8 are attached so that they extend away from the opening 9 approximately along the outer surface of the spring 2 or at an acute angle therewith.

Each finger tab 7 or 8 functions as a lever for widening the opening 9 of a slot 10 delineated by the inner, concave surface of the spring 2. The second ends 72 and 82 are grasped between thumb and forefinger and squeezed together. This causes the first ends 71 and 81 to displace away from one another. Since the first ends 71 and 81 are connected to the jaws 3 and 4, respectively, the jaws 3 and 4 separate, against the bias of the spring 2. Thus, the opening 9, separating the pressure pads 5 and 6, is widened. While in this "open" state, the tragus clip 1 is manipulated so that the tragus of the ear is inserted through the opening 9 into the slot 10, i.e., with one jaw (e.g., the jaw 3) positioned over the ear canal side of the tragus lobe and the other jaw (e.g., the jaw 4) positioned over the outer side of the tragus lobe. Once properly positioned, the pressure on the ends 72 and 82 of the finger tabs 7 and 8 is released. A restoration compression force of the spring 2 acts to press the jaws 3 and 4 together thereby causing the pressure pads 5 and 6 to clamp or pinch the tragus lobe.

In normal use, a tragus clip 1 is worn on each ear at the same time. Illustratively, the tragus clips are worn for up to three hours at a time.

It may be appreciated that the tragus clip 1 applies a clamping force to the tragus lobe, thereby affixing the clip to the tragus lobe and stimulating nerve endings thereat. The amount of force developed by the tragus clip 1 depends on its dimensions, the materials used in its construction and the size of the tragus lobe to which the tragus clip 1 is attached. It is important to design the tragus clip 1 so that it delivers the correct amount of force. If too little force is applied by the tragus clip 1, it may tend to slip off the tragus. On the other hand, too much force can readily cause headaches, queazy stomachs and sore ears.

The tragus clip 1 is illustratively designed to deliver a different clamping force in the range of approximately 0.05 to 0.15 lbs. Different users of the tragus clip 1 can tolerate different levels of force on their tragi. Some users cannot tolerate any force, no matter how light, while others can tolerate up to 0.15 lbs. of force. Illustratively, the tragus clip 1 is designed to deliver 0.10 lbs. of clamping force as this level of force can be tolerated by a large segment of the population.

When compressed, the tragus is approximately 0.125″ thick with a $5^{th}$ to $95^{th}$ percentile range of 0.106″ to 0.141″. Additionally, men, older people and overweight people have slightly, but significantly, thicker tragi. Illustratively, the tragus clip 1 is designed to deliver the same clamping force, e.g., 0.10 lbs, to the tragus over a broad range of jaw separations, which jaw separations are caused by different tragus thicknesses.

Figure 2A:
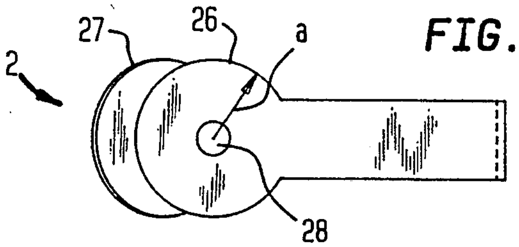
FIGS. 2*a* and 2*b* show a side and top view, respectively, of a spring of the embodiment depicted in FIG. 1 in greater detail.
Figure 2B:
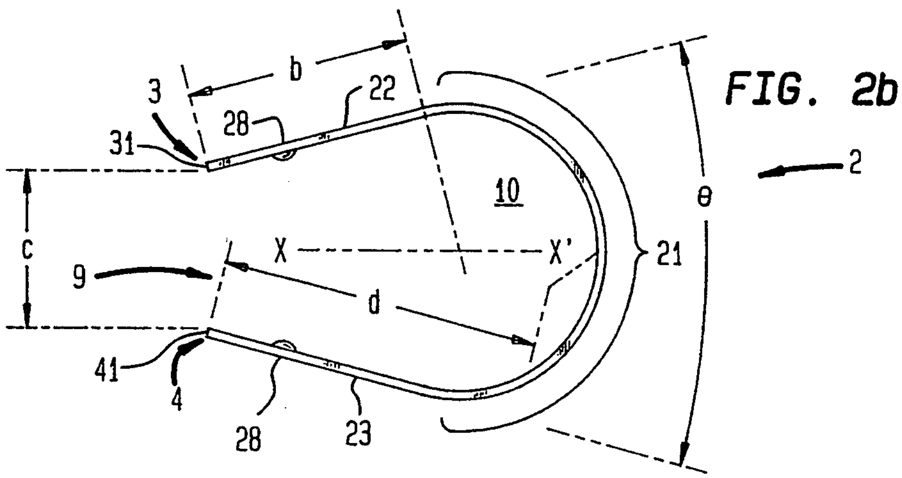

Turning now to FIGS. 2*a* and 2*b*, the spring 2 is shown in greater detail. Illustratively, the spring 2 is made out of stainless steel; however, any elastic material can be used which generates the requisite force over the range of deflections produced by the expected rage of tragus thicknesses. Stainless steel also offers an advantage in that it is easy to form.

Illustratively, the spring 2 is formed from a flat blank approximately 1.118″ in length in FIG. 2*b*, d=0.451. The blanks may have enlarged, approximately circular plates 26 and 27 on which the pads 5 and 6 (FIGS. 1*a–c* and 4*a–b*) may be affixed. Illustratively, each plate has an a=0.118″ radius. The spring 2 may also have welding dimples 28 and 29 for locating a welding point for affixing the finger tabs 7 and 8 (FIGS. 1*a–c* and 3*a–b*).

As shown, the blank is illustratively formed into a "C" shape having an axis of symmetry XX′. A "C" shape provides the simplest, most economical use of material and yields a spring with a fairly flat force-to-deflection curve over the range of installed deflections typically experienced by the spring 2.

As depicted, the "C" shaped spring 2 illustratively has an approximately semi-circular portion 21 with a radius of curvature in the range of approximately 0.12 to 0.20″, e.g., the radius of curvature may be 0.16″. The jaws 3 and 4 are formed by arms 22 and 23 which extend from the ends of this semi-circular portion 21 approximately b=0.260″ along the rays of an approximately O=29° angle. The vertex of this angle is illustratively positioned outside the slot 10 on the axis of symmetry XX′, at least some distance from the opening 9. The vertex, however, is closer to the opening 9 than the semi-circular portion 21 of the spring 2. The ends of each jaw 31 and 41 are separated by approximately c=0.180″ in a state of rest. Illustratively, these jaws 31 and 41 may be designed so that they are separated by anywhere from approximately 0.0 to 0.25″ in a state of rest. Furthermore, the spring 2 is illustratively designed so that the ends 31 and 41 may be displaced up to a approximately 0.35″ separation without permanent deformation. Illustratively, the jaw ends 31 and 41 are displaced up to an approximately 0.276″ separation during use.

The width, thickness, material and temper of the spring 2 can vary over a large range but the overall physical size, specifically, the radius of curvature of the semi-circular portion 21 and length of the arms 22 and 23, cannot. This is because large sized "C" shaped springs 2 would be obtrusive in a petite ear, while small sized "C" shaped springs 2 may not fit around large tragi.

Figure 3A:
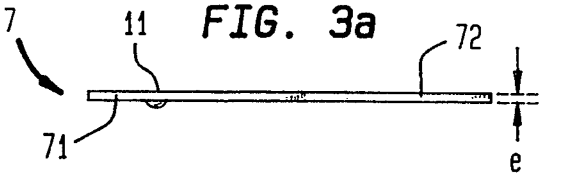
FIGS. 3*a* and 3*b* show a side and top view, respectively, of a finger tab of the embodiment depicted in FIG. 1 in greater detail.
Figure 3B:
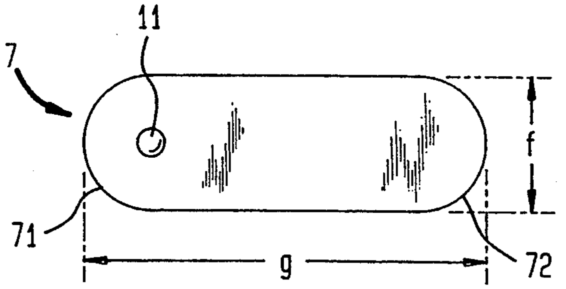
Figure 5A:
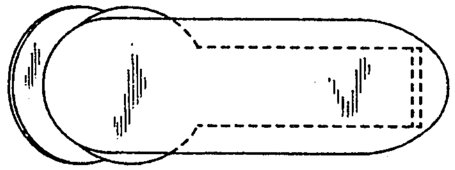
FIGS. 5*a* and 5*b* show a side and top view of an integral spring and finger tab construction according to an embodiment of the present invention.
Figure 5B:
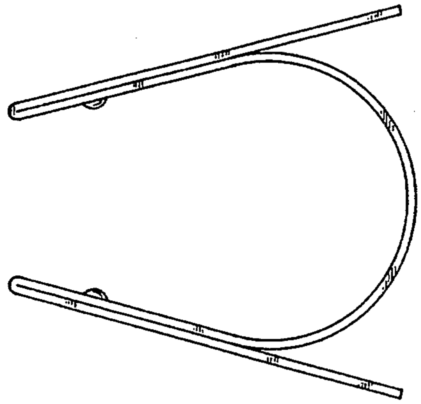

Referring now to FIGS. 3*a* and 3*b*, a finger tab, e.g., the finger tab 7, is shown. As shown, the finger tab 7 is a separate stainless steel piece which is spot welded, at the welding point 11, to the welding dimple 28 or 29 on the outer concave surface of the spring 2 (FIGS. 1*a–c* and 2*a–b*). This is only illustrative, however. In the alternative, the finger tab 7 may be made of another material, such as plastic, and may be attached in another fashion, such as by gluing. In yet another alternative embodiment, the finger tabs 7 and 8 and the spring 2 are integral which integral unit may be formed from a single flat stainless steel blank as shown in FIGS. 5*a*–5*b*.

The dimensions of the finger tabs 7 and 8 can vary greatly. A larger finger tab 7 or 8 provides greater control while it is pinched between thumb and forefinger. However, a smaller finger tab 7 or 8 can fit entirely in the ear canal without touching it. This allows the user to speak on the telephone without having to first remove the tragus clip 1 (FIGS. 1*a–c*).

Illustratively the finger tab 7 is a flat rectangular plate with semicircular ends 71 and 72. For example, the tab 7 may be g=0.45″ long, f=0.15″ wide, e=0.015″ thick and have semi-circular ends with a radius of 0.079″.

Figure 4A:
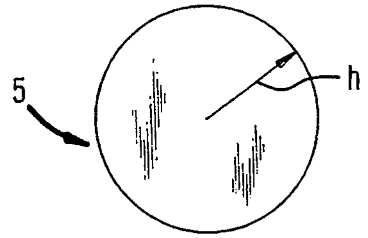
FIGS. 4*a* and 4*b* show a top and cross-sectional view, respectively, of a pressure pad of the embodiment shown in FIG. 1 in greater detail.
Figure 4B:
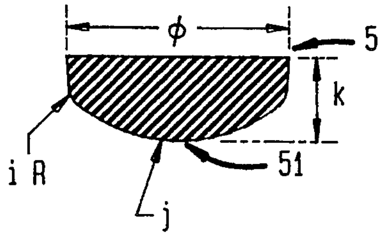

Referring now to FIGS. 4*a* and 4*b*, a pressure pad, e.g., the pressure pad 5, is shown in greater detail. The pressure pad 5 is illustratively secured to the jaw 3 (FIGS. 1*a* and 2*b*), for example, to the inner surface of the plate 26 (FIG. 2*a*), using a bonding agent such as Loctite SB 495.

The diameter, profile and softness of the pressure pad 5 all interplay to render a comfortable interface to the ear. The durometer of the material used to form the pressure pad 5 has the greatest impact on comfort. Illustratively, a material with a durometer in the range of 5 Shore A to 12 Shore A may be used. Materials below 5 Shore A in softness are too difficult to handle and too pliable to provide a uniform distribution of the pinching force of the spring 2 (FIGS. 1*a–c* and 2*a–b*). Harder materials having a durometer above 12 Shore A do not readily conform to the variations in tragus contour and therefore develop "hotspots" of discomfort. Illustratively, an elastomeric material having a 6 Shore A durometer, such as PMC-724 castable urelastomer, is used.

The spherical radius profile 51 of the pressure pad 5 provides for a normalized transfer of force from the spring 2 (FIGS. 1*a–c*) regardless of the amount of deflection of the spring 2 (FIGS. 1*a–c*), or variations in the tapered contour of the tragus, between its interior and exterior surfaces. Illustratively, the spherical radius profile 51 has a j=0.180″ spherical radius.

As depicted, the spherical radius profile 51 illustratively extends from a tapered cylinder, or base portion of an approximately conical cross-section having a 0 4° angle. The zenith of the spherical profile extends k=0.095″ above the bottom of the pressure pad 5, which bottom is affixed to the inner surface of the spring 2 (FIGS. 1*a–c*).

The diameter of the pressure pad 5 is chosen to be in the range of approximately h=0.18″ to 0.38″. A larger pressure pad 5 would entirely cover most tragus lobes but could not be securely attached to a small tragus. Furthermore, a larger pressure pad 5 would require a heavier spring 2 (FIGS. 1*a–c* and 2*a–b*) in order to maintain consistent pad pressure, which heavier spring 2 (FIGS. 1*a–c* and 2*a–b*) would encroach on the comfort of the user. On the other hand, a smaller radius pressure pad 5 would not be as effective in stimulating nerve endings on a larger tragus. Furthermore, a smaller pressure pad 5 would require a lighter spring 2 (FIGS. 1*a–c* and 2*a–b*) in order to maintain a consistent pad pressure, which lighter spring 2 may compromise the ability of the tragus clip 1 (FIGS. 1*a–c*) to remain affixed to the tragus. Illustratively, the pressure pad 5 has a i=0.250" radius.

In summary, a tragus acupressure clip is disclosed which is easy to manufacture and convenient to use. The tragus clip is designed for effective and comfortable use by a wide segment of the population.

Finally, the aforementioned discussion is intended to be merely illustrative. Numerous other embodiments of the present invention may be devised by those having ordinary skill in the art without departing from the spirit or scope of the following claims.

We claim:

1. A tragus clip comprising:

a concave spring having two opposing jaws separated by an opening of a slot delineated by an inner surface of said concave spring, two opposing pressure pads for stimulating nerve endings of said tragus, each positioned on the end of a different jaw, on said inner surface of said spring, and separated by said slot, two mutually non-touching finger tabs, each having one end attached to the end of a different jaw, on an outer surface of said spring and having a second end extending away from said end of said jaw, along said outer surface of said spring approximately only as far as a portion of said spring opposite to said opening separating said jaws, whereby said second ends of said finger tabs are urged towards one another, against a compression bias of said spring to enlarge said slot separating said pressure pads.

2. The tragus clip of claim 1 wherein said concave spring is approximately C-shaped, having an approximately semi-circular portion with an arm extending from each end of said approximate semi-circle along rays of an acute angle having a vertex outside of said C-shape but closer to said arms than said semi-circle said arms forming said jaws.

3. The tragus clip of claim 2 wherein said C-shape of said spring has a radius of curvature between approximately 0.12" and 0.20".

4. The tragus clip of claim 3 wherein said C-shaped spring has a radius of approximately 0.16".

5. The tragus clip of claim 2 wherein said acute angle is approximately 29°.

6. The tragus clip of claim 1 wherein, during a state of rest, said jaws of said spring are separated by a distance in the range of approximately 0.0" to 0.25".

7. The tragus clip of claim 6 wherein said ends of said jaws are separated by 0.180" when said spring is in a state of rest.

8. The tragus clip of claim 6 wherein said ends of said jaws are capable of experiencing a separation of up to approximately 0.35" without permanently deforming said spring.

9. The tragus clip of claim 1 wherein said spring is made of stainless steel.

10. The tragus clip of claim 1 wherein said spring is made of plastic.

11. The tragus clip of claim 1 wherein said finger tabs are secured to said outer surface of said spring by a welding.

12. The tragus clip of claim 1 wherein said finger tabs are glued to said outer surface of said spring.

13. The tragus clip of claim 1 where said finger tabs are integral with said spring.

14. The tragus clip of claim 1 wherein said tabs are small enough to fit in, without touching, an ear canal when said tragus clip is secured to a tragus lobe.

15. The tragus clip of claim 1 wherein said pressure pads have a durometer between approximately 5 Shore A and 12 Shore A.

16. The tragus clip of claim 15 wherein said durometer is 6 Shore A.

17. The tragus clip of claim 1 wherein said pressure pads are made of an elastomeric material.

18. The tragus clip of claim 1 wherein said pressure pads are capable of contacting a tragus lobe and providing a normalized transfer of clamping force from said spring over a range of jaw separations.

19. The tragus clip of claim 1 wherein said pressure pads have a spherical profile extending perpendicularly from said inner surface of said spring.

20. The tragus clip of claim 1 wherein said pressure pads have an approximately circular cross-section in parallel with said inner surface of said sprint having a radius approximately between 0.18" and 0.38".

21. The tragus clip of claim 20 wherein said radius is 0.250".

22. The tragus clip of claim 1 wherein said spring applies a pinching force in the range approximately 0.05 lbs to 0.15 lbs when said tragus clip is attached to a tragus.

23. The tragus clip of claim 22 wherein said spring applies approximately 0.10 lbs of pinching force.

24. The tragus clip of claim 1 wherein information is printed on said outer surface of said spring.

25. The tragus clip of claim 1 wherein said spring is entirely disposed between opposing surfaces of said finger tabs.

* * * * *